United States Patent [19]

Mesch

[11] Patent Number: 4,803,281

[45] Date of Patent: Feb. 7, 1989

[54] PREPARATION OF 4-METHYLIMIDAZOLE

[75] Inventor: Walter Mesch, Ludwigshafen, Fed. Rep. of Germany

[73] Assignee: BASF Aktiengesellschaft, Ludwigshafen, Fed. Rep. of Germany

[21] Appl. No.: 129,711

[22] Filed: Dec. 7, 1987

[30] Foreign Application Priority Data

Dec. 12, 1986 [DE] Fed. Rep. of Germany ....... 3642484

[51] Int. Cl.$^4$ ........................................... C07D 233/58
[52] U.S. Cl. .................................................. 548/335
[58] Field of Search ........................................ 548/335

[56] References Cited

U.S. PATENT DOCUMENTS 3,030,376 4/1962 Liggett et al. ...................... 548/335
4,074,054 2/1978 Christidis et al. .................. 548/335
4,377,696 3/1983 Graf .................................... 548/335

OTHER PUBLICATIONS

Bredereck et al. *Chem. Ber.*, vol. 86, pp. "88-96", 1953.
Chem. Berichte, 2706 (1882).
Angewandte Chemie, 71 759 (1959).

*Primary Examiner*—Mary C. Lee
*Assistant Examiner*—Zinna Northington
*Attorney, Agent, or Firm*—John H. Shurtleff

[57] ABSTRACT

A process for the preparation of 4-methyl-imidazole by the reaction of hydroxypropanone and formamide, in which the reaction is carried out in the presence of at least twice the molar amount of ammonia, based on hydroxypropanone, in the liquid phase at temperatures of from 100° to 200° C. and pressures of from 10 to 250 bar.

10 Claims, No Drawings

PREPARATION OF 4-METHYLIMIDAZOLE

The present invention relates to a novel process for the preparation of 4-methylimidazole from hydroxypropanone, formamide, and ammonia.

4-Methylimidazole, an important intermediate, e.g. for the preparation of pharmacologically effective end products, is prepared industrially by the reaction of methylglyoxal, formaldehyde, and excess ammonia. Only moderate yields are obtained by this process, which corresponds to Radziszewski's synthetic route (Chem. Ber., 2706 (1882)).

Only minor amounts of 4-methylimidazole are obtained if one attempts to prepare it from α-hydroxyketone and formamide as in the imidazole synthesis described in Angew. Chem., 71, 759 (1959).

It was found that, surprisingly, 4-methylimidazole of high purity is obtained in high yield by reacting hydroxypropanone and formamide in the presence of an addition to the reaction mixture of at least twice the molar amount of ammonia, based on the amount of hydroxypropanone, in the liquid phase at temperatures of from 100° to 200° C. and pressures of from 10 bar to 250 bar, preferably 20 to 50 bar.

In the process according to the invention the relative amounts of the reactants are so chosen that for every mole of hydroxypropanone 1 to 10 moles, preferably 1 to 8 moles, and especially 1 to 4 moles of formamide and at least 2 moles, preferably at least 4 moles, especially at least 10 moles (e.g. 50 to 90 moles) of ammonia are employed. Since the reaction is preferably carried out in liquid ammonia, the ratio of the amount of ammonia to the amount of hydroxypropanone can be, for instance, up to 100 moles:1 mole.

The reaction is carried out at temperatures of from 100° to 200° C., preferably at from 140° to 180° C. The vapor pressure of the liquid ammonia in the mixture requires that the reaction is carried out in a pressure reactor. The pressures reached are between 10 bar and 250 bar, particularly 20 to 50 bar. Reaction times range from 30 min to 120 min. An autoclave is used for batchwise working. Preferably the reaction between the three substances is carried out continuously, in a pressure tube for instance. The liquid ammonia is added under pressure, or the other two components are added to the liquid ammonia, separately or together. The reaction mixture is worked up by, for instance, fractional distillation. The new process gives 4-methylimidazole of high purity in high yield in a technically simple way.

EXAMPLE 1 (Comparison)

Formamide (270 g, 6 moles) is placed in a flask with stirrer and heated to 140° C. Hydroxypropanone (148 g, 2 moles) is added dropwise, with stirring. The reaction mixture is stirred for 3 h. A dark-brown reaction product is obtained that is found by gas chromatographic analysis to contain 7 g of 4-methylimidazole (corresponding to 4% yield).

EXAMPLE 2 (Comparison)

Formamide (270 g, 6 moles) is placed in a flask with stirrer and heated to 140° C. At a pressure of 150 mbar hydroxypropanone (148 g, 2 moles) is added dropwise, and at the same time 60 g of water, mixed with a little hydroxypropanone, is distilled off via a fractionating column. A dark-brown reaction product is obtained that is found by gas chromatographic analysis to contain 8 g of 4-methylimidazole (corresponding to 5% yield).

EXAMPLE 3

Formamide (270 g, 6 moles) and hydroxypropanone (148 g, 2 moles) are placed in a stirred 2-liter autoclave. Liquid ammonia (340 g, 20 moles) is pumped in. The temperature is raised to 140° C., whereupon the pressure rises to 50 bar, and maintained for 3 h. The autoclave pressure is then released and the reaction mixture obtained is distilled overhead. At 10 mbar a pale-yellow fraction passes over between 130° C. and 200° C. It is found by gas chromatographic analysis to contain 60 g of 4-methylimidazole, corresponding to 37% yield.

EXAMPLE 4

A mixture of hydroxypropanone (32 g, 0.43 mole) and formamide (153 g, 3.4 moles) as well as liquid ammonia (800 ml, 47 moles) is pumped uniformly at 200 ml/h in a tube reactor of 1 liter capacity, flow being from bottom to top. The temperature of the reaction mixture is maintained at 160° C. The reactor output is freed from ammonia by heating it to 100° C. The pale-yellow distillate obtained by overhead distillation of 1000 g of the crude product contains 127 g of 4-methylimidazole. This corresponds to 81% yield.

If the crude product is rectified with a 30-cm packed column the fraction passing over at from 136° C. to 140° C. and 12 mbar yields 4-methylimidazole in the form of colorless crystals that melt at 51° C.

I claim:

1. A process for the preparation of 4-methylimidazole which comprises:
   reacting hydroxypropanone and formamide in the presence of an addition to the reaction mixture of at least twice the molar amount of ammonia, based on the amount of hydroxypropanone, the reaction being carried out in the liquid phase at temperatures of from 100° to 200° C. and pressures of from 10 to 250 bar.

2. A process as claimed in claim 1 wherein the reaction is carried out at temperatures of from 140° to 180° C. and pressures of from 20 to 50 bar.

3. A process as claimed in claim 1 wherein 1 to 10 moles of formamide are used per mole of hydroxypropanone.

4. A process as claimed in claim 1 wherein 1 to 8 moles of formamide are used per mole of hydroxypropanone.

5. A process as claimed in claim 1 wherein at least 4 moles of ammonia are used per mole of hydroxypropanone.

6. A process as claimed in claim 1 wherein at least 8 moles of ammonia are used per mole of hydroxypropanone.

7. A process as claimed in claim 1 wherein at least 10 moles of ammonia are used per mole of hydroxypropanone.

8. A process as claimed in claim 1 wherein the reaction is carried out at temperatures of from 140° to 180° C. and pressures from 20 to 50 bar, using 1 to 10 moles of formamide per mole of hydroxypropanone and at least 4 moles of ammonia per mole of hydroxypropanone.

9. A process as claimed in claim 8, using at least 8 moles of ammonia per mole of hydroxypropanon.

10. A process as claimed in claim 8, using at least 10 moles of ammonia per mole of hydroxypropanone.

* * * * *